United States Patent [19]
Labouze

[11] Patent Number: 5,624,406
[45] Date of Patent: Apr. 29, 1997

[54] SYRINGE FOR ADMINISTERING A GIVEN NUMBER OF INJECTIONS

[75] Inventor: Joseph Labouze, Soisy-sous-Montmorency, France

[73] Assignee: S.C.E.R. Securingue (Society Civile), Paris, France

[21] Appl. No.: 500,901

[22] PCT Filed: Jan. 28, 1994

[86] PCT No.: PCT/FR94/00107

§ 371 Date: Jul. 28, 1995

§ 102(e) Date: Jul. 28, 1995

[87] PCT Pub. No.: WO94/16753

PCT Pub. Date: Aug. 4, 1994

[30] Foreign Application Priority Data

Jan. 29, 1993 [FR] France ................... 93 00988
Apr. 29, 1993 [FR] France ................... 93 05108

[51] Int. Cl.$^6$ ................................................ A61M 5/00
[52] U.S. Cl. ......................... 604/207; 604/110; 604/218
[58] Field of Search ............................ 604/207–210, 604/218, 228, 219, 220, 223, 224, 229, 110, 198, 272

[56] References Cited

U.S. PATENT DOCUMENTS

| | | | |
|---|---|---|---|
| 4,518,383 | 5/1985 | Evans | 604/51 |
| 4,978,339 | 12/1990 | Labouze et al. | 604/110 |
| 5,007,903 | 4/1991 | Ellard | 604/195 |
| 5,021,047 | 6/1991 | Movern | 604/110 |
| 5,037,394 | 8/1991 | Mazurik et al. | 604/110 |
| 5,158,549 | 10/1992 | McCarthy | 604/110 |
| 5,250,030 | 10/1993 | Corsich | 604/110 |

FOREIGN PATENT DOCUMENTS

| | | |
|---|---|---|
| 0339954 | 11/1989 | European Pat. Off. . |
| 0376698 | 4/1990 | European Pat. Off. . |
| 3833138 | 4/1990 | Germany . |

*Primary Examiner*—V. Millin
*Assistant Examiner*—V. Alexander
*Attorney, Agent, or Firm*—Lowe, Price, LeBlanc & Becker

[57] ABSTRACT

Syringe consisting of a body in which is disposed a piston (2) of the kind including at least two racks (53, 54) fitting onto the body and at least one lug carried by the piston (2), each of the racks being capable of being shifted in a single direction in relation to a lug. According to the invention, the syringe includes two lugs (63, 64) carried by a yoke (6) which straddles the piston (2), and is rotatably movable about the piston's axis. The lugs (63, 64) are driven into translation by the piston (2) while rotating freely in relation to the latter.

16 Claims, 4 Drawing Sheets

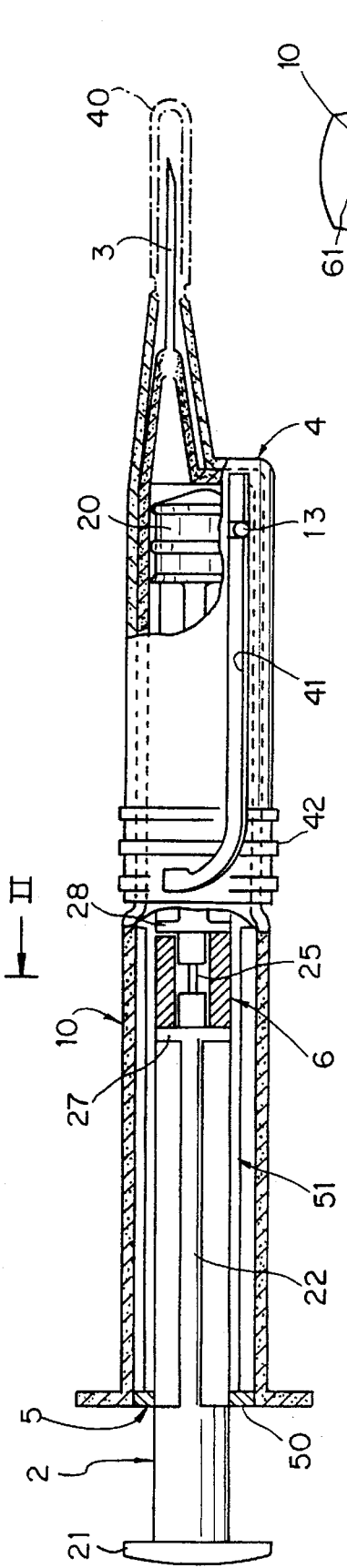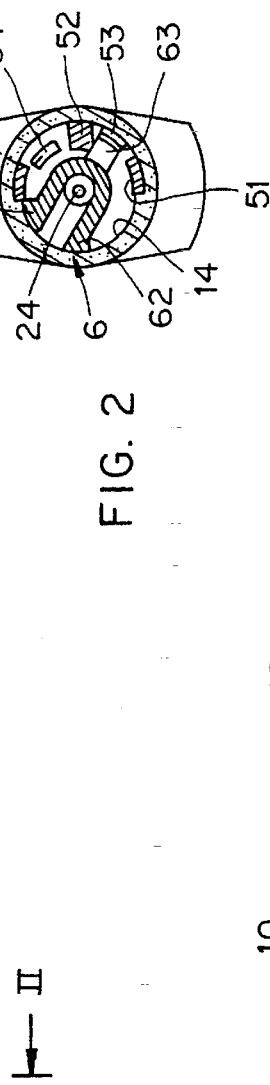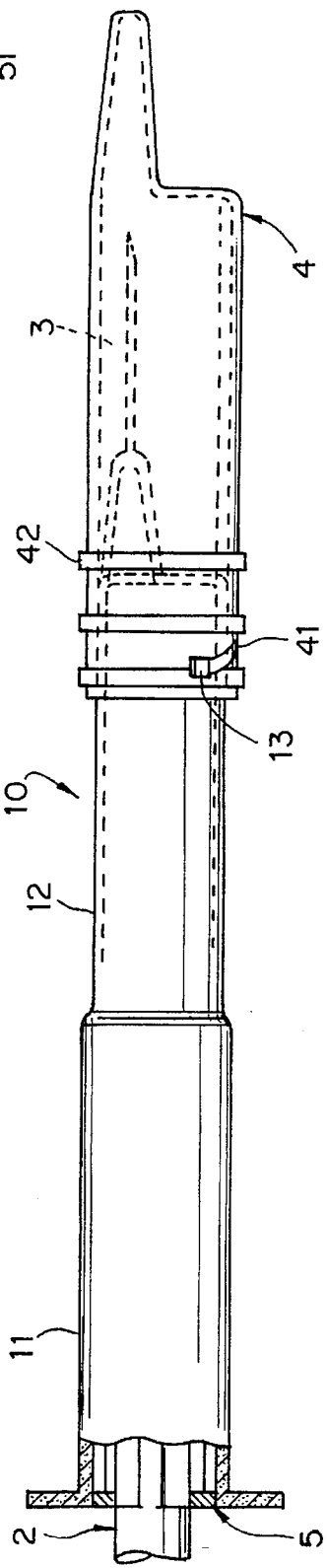
FIG. 1
FIG. 2
FIG. 6

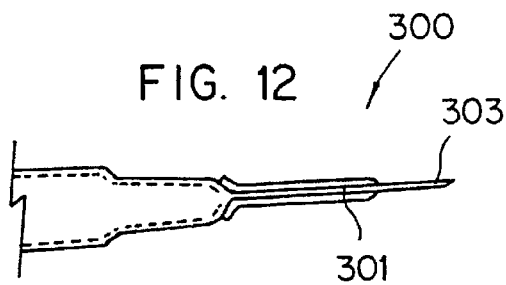
FIG. 12
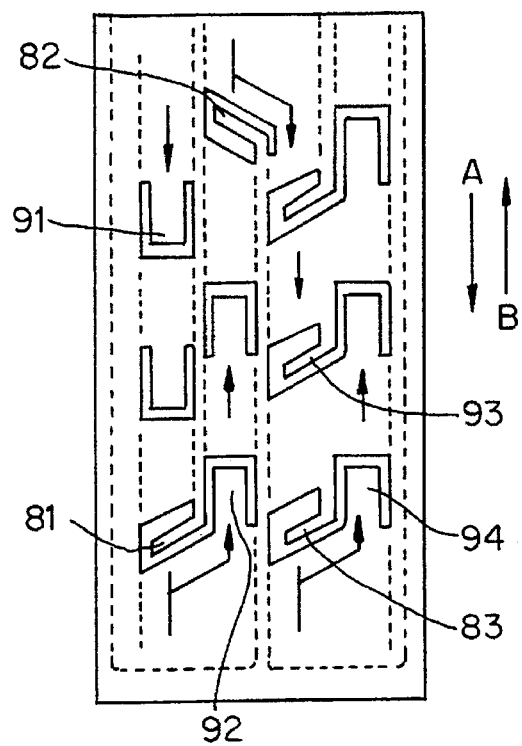
FIG. 10
FIG. 9
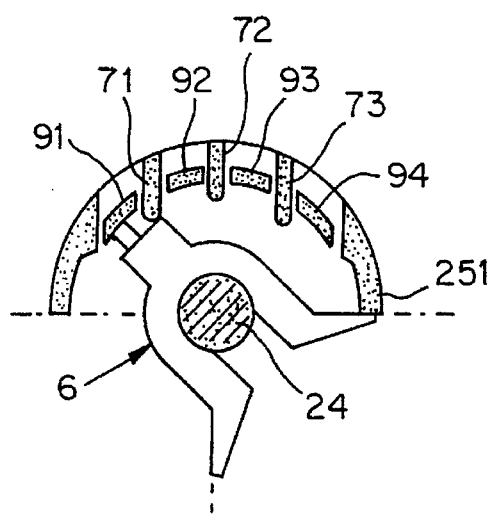
FIG. 11
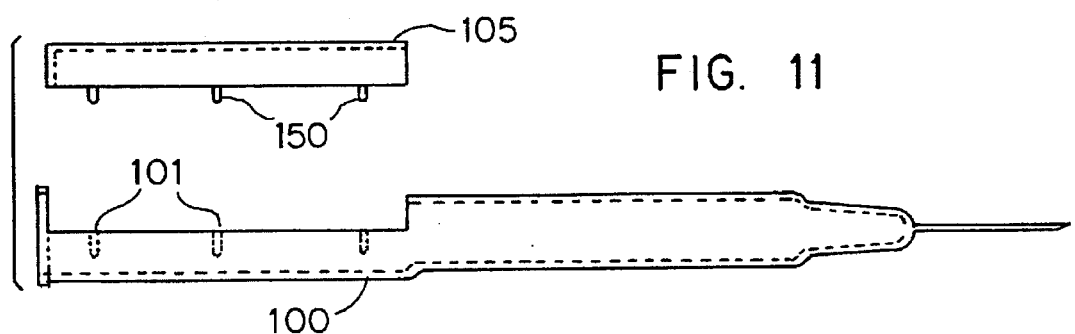

5,624,406

SYRINGE FOR ADMINISTERING A GIVEN NUMBER OF INJECTIONS

FIELD OF THE INVENTION

This invention relates to a syringe in general and more particularly to a syringe for administering a given number of injections, with the possibility of limiting this number to one.

BACKGROUND ART

For numerous years, in view of the proliferation of diseases transmissible by blood, assiduous attempts have been made to market syringes enabling just one injection to be administered and that are fully reutilization-proof.

Though a very large number of propositions have been made, to date none of these has proved fully satisfactory.

It is usually proposed that use be made of units comprising racks formed on the piston of the syringe and cooperating with one or more studs integral with said syringe body, so as to allow relative motion in one direction and to prohibit any motion in the opposite direction.

There has also been proposed, in document EP 0 339 954, a syringe of which the piston bears studs or lugs, whereas the racks are formed on the body of the syringe.

To use these syringes, the piston is pulled outwardly from the syringe body, a rack thus moves before the stud enabling the piston to move outwards, said rack being shaped so as to prevent any return motion of said piston towards the interior of the syringe body. After filling the body of the syringe during this outward pulling movement of the piston, the piston must be rotated through a given angle in order to bring the second rack into relation with the same stud or with a second stud. In this position, the second stud allows the piston to descend to the bottom of the syringe body but prohibits any withdrawal motion of said piston.

When the piston is thus returned to the bottom of the syringe body, it is no longer possible to rotate it about itself and it is also impossible to remove it from said body due to the blocking engagement of the rack and the second stud.

The utilization of a syringe of this type is complex due to the fact that the piston must be made to rotate about itself through a given angle before ejecting the product drawn into the syringe.

There has also been proposed, in document DE 38 33 138, a single-usage syringe of which utilization is, from the user's point of view, perfectly similar that of usual syringes. This syringe has an insert mounted rotatably mobile within the syringe body. The insert can bear either lugs cooperating with racks formed on the piston, or racks cooperating with lugs borne by the piston. One of the racks is slanted at an angle to the axis of the syringe so as to rotatably drive the insert when the piston is drawn out and to bring the rack and lug into cooperation so as to enable the piston to be pressed in.

These arrangements have the drawback of being subject to working poorly as a result of the frictional forces at play between the syringe body and the insert and preventing said insert from rotating.

Furthermore, it has been observed that the single-usage syringes provided usually have a drawback consisting in the fact that, when they are used, the piston must be pulled back to the end of its outward stroke from the syringe prior to performing the manipulations required to enable injection and the second rack to be brought into play.

This invention also tends to provide a syringe enabling the user to perform intermediary dosages, i.e., not to completely draw out the piston before the injection.

This syringe will thus enable the injection of a variable quantity of product, and yet prohibit any further injection thereafter.

Moreover, it has been observed that the utilization of syringes only authorizing one single injection requires, in certain cases, the utilization of two or more syringes for the same treatment.

There are, in fact, a certain number of products of which the utilization requires that a liquid and a powder be mixed together for prior constitution of a solution to be injected subsequently.

This invention thus tends to provide a syringe which, depending on its constitution, will enable a predetermined number of injections to be administered, one in the case of conventional utilizations, or two or more for special utilizations during treatment or laboratory analyses.

SUMMARY OF THE INVENTION

The object of this invention is to provide a syringe for administering a given number of injections, consisting of a body in which is disposed a piston, of the kind comprising two racks fitted onto the body and at least one lug borne by the piston, each of said racks being capable of being shifted in a single direction in relation to a lug, characterized in that it comprises two lugs borne by a yoke which straddles the piston and is rotatably mobile about the axis of said piston, said lugs being driven in translation by the piston while rotating freely in relation to the latter.

The syringe according to the invention is further remarkable in that:

—the rack enabling withdrawal of the piston comprises at least one oblique tongue slanted in relation to the axis of the syringe so as to allow it to be passed over by the lugs of the yoke when the piston is drawn out, and to impress upon the yoke, during the pushing in of the piston, a rotating motion so as to position the lugs of the yoke opposite the tongues of the second rack in such a way that the pushing in of the piston will be possible after the lugs of each of the oblique tongues of the first rack have been passed over;

—it comprises several couples of alternate racks, the first rack allowing the piston to move outwards from the body of the syringe, and the last rack enabling the piston to be driven back towards the bottom of the syringe body, and oblique tongues situated at the end of each rack excepting the last one to ensure the rotation of the yoke so that the lugs cooperate with the next rack every time the direction of displacement of the piston is reversed;

—the even-ranking racks have transversal tongues, and at least one of the odd-ranking racks has oblique tongues;

—the yoke is of globally U-shaped cross section and bears said lugs on its outer side in the rounded portion of the "U" shape;

—the ends of said "U" shape are bordered by ribs on their outer surfaces;

—at least one of the two lugs is tapered in the direction of the axial end of the yoke;

—the racks are formed on an insert fitted onto the body of the syringe;

—the insert is comprised of a semi-cylindrical body ended by an end plate perpendicular to it;

—the body of the insert is separated, by a longitudinal rib disposed on its inner wall ending in a curved tip extending into a recess, into two parts each bearing a series of tongues whose ends protrude from the inner wall in the direction of the axis in order to confer upon said body a longitudinal section in the shape of racks;

—the curved tip has its end disposed longitudinally to the front of the tongues forming the rack;

—the piston comprises two portions connected together by a cylindrical axial rod;

—said cylindrical axial rod is separated into two parts by a fragile link;

—the diameter and length of said axial rod are such that the yoke can be positioned thereupon in such a way as to straddle it;

—the distance axially separating the inner side of the end plate of the insert from the end of the curved tip is greater than the length of the yoke so that, when the outward pulling motion of the piston is completed, the yoke is completely disposed between the end plate and said tip extends axially in the prolongation of the lugs, and so that, during the return motion of the piston towards the inside of the syringe body, the lug comes into contact with said curved tip and rotates the yoke to bring the lugs into the axis of the tongues forming the rack, without the piston being rotated;

—it bears a double needle constituted by two needles of which one is inserted into the other, a thin internal needle welded to the end of the syringe body and a removable needle of larger diameter positioned around said thin needle so as to administer to the patient the injection with the thin needle.

BRIEF DESCRIPTION OF THE DRAWINGS

Further features and advantages of the invention will be apparent from the following description of the invention given, by way of a non-limiting example, in reference to the corresponding accompanying drawings in which:

FIG. 1 is a partially longitudinal section of the syringe embodying the invention;

FIG. 2 is a cross sectional view along line II—II of FIG. 1 for a syringe enabling just one injection to be administered;

FIG. 6 represents the syringe after utilization;

FIG. 9 is a view similar to FIG. 2 of a syringe enabling two injections to be administered;

FIG. 10 is a detailed view of the body of the insert for a syringe enabling two injections to be administered;

FIG. 11 schematically shows an embodiment of the syringe.

FIG. 12 schematically shows a double needle syringe.

DESCRIPTION OF THE PREFERRED EMBODIMENT

Figure 3:
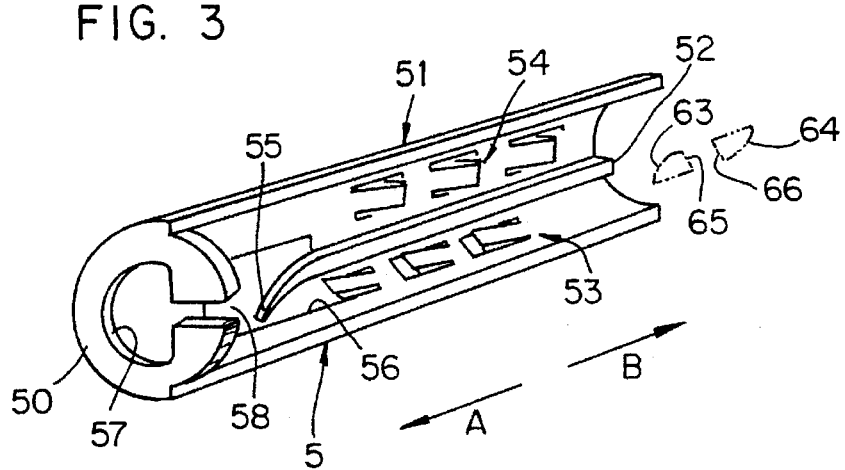
FIG. 3 is a perspective view of the insert.

It can be seen in FIG. 1 that the syringe embodying the invention comprises, in a known manner, a syringe body 10 inside which is disposed a piston 2 having a tightness liner 20 at its end disposed inside the body 10, and a push plate 21 at its end disposed outside the body 10.

The body 10 also bears a needle 3 and a cover 4 protecting this needle.

In a known manner, said cover 4 comprises an end portion 40 that can be removed to reveal the needle 3 for the purpose of using the syringe.

As can be seen in FIG. 3, the insert 5 is constituted, in the example represented, of a body in the shape of a semicylinder ended by an end plate perpendicular thereto. Such a semicylindrical body is preferred so as to reduce the quantity of material used and to facilitate the manufacturing of the insert by moulding.

The circumference dimension of said body 51 can be modified and depends, as will be understood from the following description, on the number of injections one wishes to authorize and on the diameter of the syringe.

Figure 5:
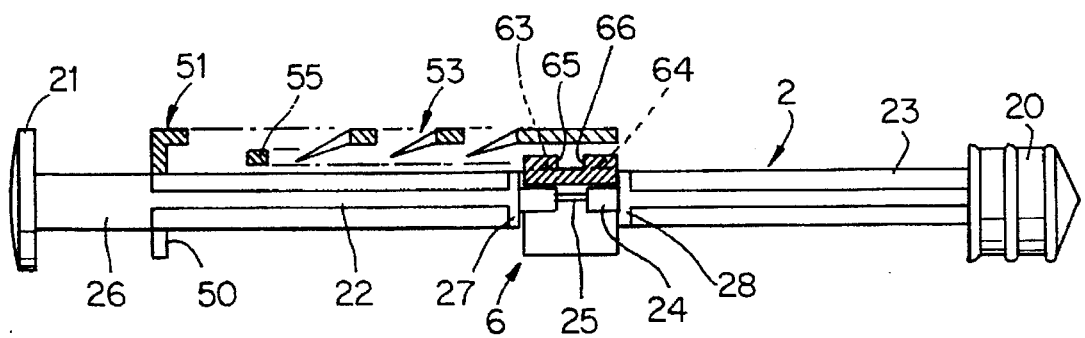
FIG. 5 is a partially longitudinal section of the piston bearing the yoke and positioned inside the insert.

The body 51 is separated into two parts by a longitudinal rib 52 disposed on its inner wall and ending in a curved tip 55 extending into a recess 56. This curved tip 55 is, as represented in FIG. 5, disposed at a distance from the outer wall of the insert.

Each part of the body 51 of the insert bears a series of tongues whose ends protrude from the inner wall in the direction of the axis. Each series of tongues confers upon the body of the insert a rack-shaped longitudinal section. The rack 53 is formed by tongues arranged with their end sides pointed towards the end plate 50, whereas the rack 54 is constituted by tongues pointing in the opposite direction.

The curved tip 55 is such that its end is disposed longitudinally to the front of the tongues forming the rack 53.

The end plate 50 comprises an opening 57 that opens out, in the embodiment represented, on the periphery of said plate 50 via a groove 58.

In FIG. 3, the opening 57 is rounded, the diameter of the rounded part being equal to that of the rod of the piston 2.

Figure 4:
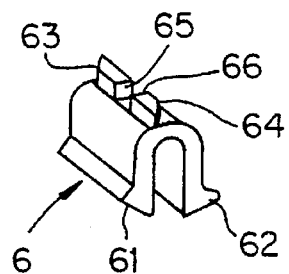
FIG. 4 is a perspective view of the yoke.

The yoke 6 used in the syringe embodying the invention has, as can be seen in FIG. 4, a globally U-shaped cross section. The ends of said "U" are bordered on their outer surfaces by ribs 61 and 62.

The yoke 6 also comprises lugs 63, 64 disposed longitudinally on its outer side in the rounded part of the "U".

The two lugs 63, 64 are tapered in the direction of the axial ends of the yoke 6.

Said lugs 63, 64 can be such as those represented in FIG. 4 or can be of shape resembling that of a diagonal rib.

As will be explained hereinafter, only one of these lugs need necessarily be tapered, though both lugs will preferably be tapered for the practical purposes of assembling the syringe embodying the invention. The facing ends 65, 66 of the lugs are comprised of flat sides perpendicular to the axis of the yoke 6.

The constitution of the piston 2 of the syringe embodying the invention will now be described in reference to FIG. 5.

The pistons of syringes usually have a rod of cross-shaped section formed by four ribs positioned perpendicularly to one another.

This usual arrangement is retained, in the embodiment illustrated, for two portions 22 and 23 of the piston 2 rod, though any other sectional shape can, of course, be used. In the example represented, a cylindrical portion 26 is formed between the push plate 21 and the first cross-shaped portion 22.

Said cross-shaped portions 22 and 23 are connected to one another by a cylindrical axial rod of smaller diameter 24 that can, as represented, be separated into two parts by a fragile link 25 of very small diameter.

Circular plates 27, 28 perpendicular to the axis of the piston are arranged between each of the two cross-shaped portions 22, 23 and the axial rod 24.

The diameter and length of said axial rod 24 are such that the yoke 6 can be positioned thereupon so as to straddle it while rotating freely about the axis of the piston and while being axially maintained by the circular plates 27, 28.

The insert 5 is positioned around the cross-shaped part 22 by inserting three ribs of the latter into the opening 57 while the fourth rib is in the groove 58 of the end plate 50.

The positioning of the piston rod in the opening of the end plate of the insert 5 can be performed by recourse to the elasticity of the materials selected to manufacture the insert 5 by moulding.

Figure 8:
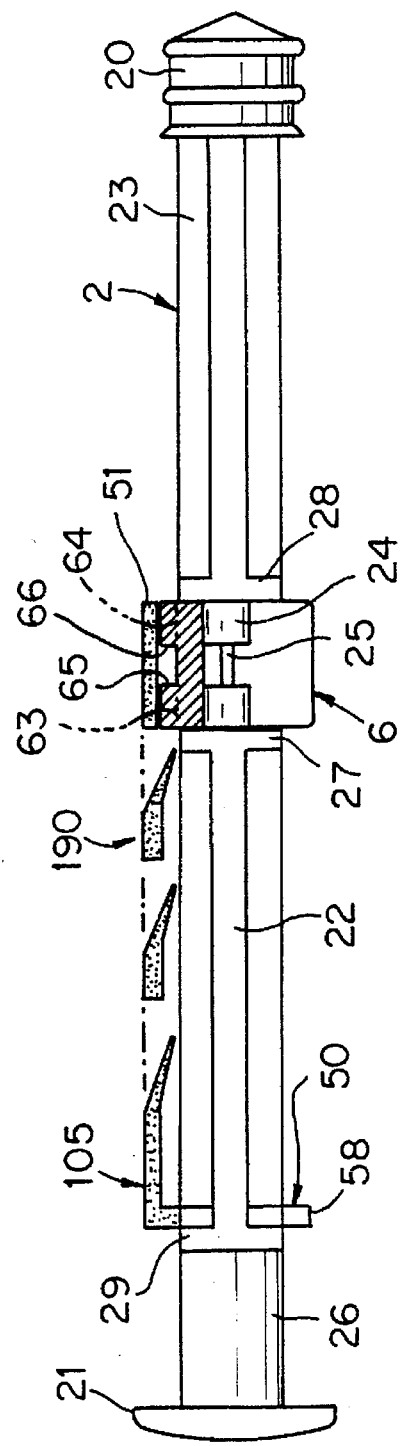
FIG. 8 is a partially longitudinal section of the piston bearing the yoke positioned in the insert.

It is also possible to provide notches, in two diametrically opposite ribs of the piston rod, so as to form a flat diametrical portion 29 such as the one that can be seen in FIG. 8. In this case, the piston 2 is positioned in the insert 5 by sliding said flat diametrical portion 29 in the groove 58.

During assembly, the insert 5 is positioned around the rod of the piston bearing the yoke 6 in such a way that the rib 61 leans against the edge of the body 51 of said insert while the lugs 63, 64 are axially aligned with the tongues forming the rack 53. This position is represented in FIG. 2 which shows the syringe after utilization.

As can also be seen in this FIG. 2, the inner surface of the syringe body is formed with a diameter slightly smaller over one half 14 of its surface in order to facilitate the positioning of the insert 5 in the syringe body. The latter can thus be arranged in abutment against the longitudinal walls bordering this half 14 of smaller diameter. The insert is then fitted onto the syringe body e.g., by rendering the end plate 50 integral by gluing, welding, etc.

The piston 2 fitted with the yoke 6 can then be displaced inside the insert 5 fitted onto the body 4 of the syringe.

As usual when using a syringe, the piston 2 is firstly pulled outwards from the syringe body in order to fill said body 10.

During this movement, the lugs 63, 64 of the yoke 6 slide along the tongues forming the first rack 53 by moving in the direction A represented in FIG. 3. Any reverse motion of the piston 2 during the filling is blocked by the abutment of the flat end 65 of the lug 63 against the end of one of the tongues forming said rack 53.

The outward motion of the piston 2 is continued until the yoke 6 comes into contact with the inner side of the end plate 50 of the insert 5, the tip 55 moving laterally and outwardly aside into the free space situated at the level of the insert wall when the lugs pass against it.

The distance axially separating the inner side of the end plate 50 from the end of the curved tip 55 is provided slightly greater than the length of the yoke 6.

In this manner, when the piston 2 is at the end of its outward stroke, the yoke 6 is entirely situated between the end plate 50 and said tip 55.

As the tip is curved in such a way that its end is disposed to the front of the tongues forming the rack 53, the latter extends axially in the prolongation of the lugs 63, 64.

By way of this arrangement, when the user pushes the piston 2 back inside the body 10 of the syringe so as to expel its contents, the lug 64 comes into contact with the curved tip 55.

For a better understanding of the invention, the lugs 63, 64 have been represented in broken lines in FIG. 3.

As the lug 64 is tapered, it can slide along the curved tip 55, thereby rotating the yoke 6 about the rod 24 until its takes up a position that is symmetrical, in relation to the diametrical plane passing through the rib 52, with the position in which it is represented in FIG. 2.

As previously suggested, it will be understood that only lug 64 need be tapered in order to cooperate with the curved tip 55. The two lugs will preferably be formed in the same way, thereby avoiding having to search for the direction in which the yoke 6 must be positioned on the piston 2.

In this new position, the rib 62 abuts against the edge of the body 51 whereas the lugs 64 and 63 are arranged in the axis of the tongues forming the rack 54.

The piston 2 can then be pushed back in direction B while any outward pulling motion in direction A is blocked by the leaning of the side 66 of the lug 64 against the end of one of the tongues forming the rack 54.

The length separating two similarly pointed ends of the lugs borne by the yoke is provided largely different to the length separating the ends of two successive tongues so as to ensure that only one of the sides 65 or 66 comes into contact with the end of one tongue without risking interference from the lug not concerned. Preferably, the yoke is provided shorter than the length separating the ends of two consecutive tongues.

As will have been understood from the foregoing description, from the user's point of view the manipulation of the syringe embodying the invention is perfectly identical to that of conventional syringes. The switching from one rack to the other is performed by rotation of the yoke and is not visible to the user.

Thus, the utilization of the racks fitted onto the syringe body, while the lugs intended to cooperate with these racks are borne by the piston so as to be translated and rotatably mobile in relation to the latter, enables the providing of a single-usage syringe that can be manipulated perfectly simply and safely while further avoiding any jarring problems due to excessive friction.

Irrespective of the position of the piston in relation to the syringe body 10 during the motion tending to push it towards the bottom of said body, all outward pulling motion is blocked as previously described. Should the user attempt to overcome this blocking, the fragile link 25 will break, thus rendering the syringe definitively unusable.

The syringe embodying the invention comprises other arrangements that will now be described.

As can be seen in FIG. 6, the body 10 of the syringe is comprised of two cylinders 11 and 12 placed end to end.

The cylinder 11 is of slightly larger diameter than the cylinder 12. This difference in diameter corresponds globally to the thickness of the body 51 of the insert 5.

The liner 20 of the piston 2 is disposed in the cylinder 12 and adapted to slide tightly along the inner wall thereof.

The cylinder 11 is of length substantially equal to that of the insert and is disposed against the inner wall of said cylinder 11.

Said cylinders 11 and 12 are of substantially equal length, the yoke 6 and the piston liner 20 also being of the same length.

Thus, when the piston is drawn out until the yoke comes into contact with the end side of the insert, the tightness liner runs the length of the cylinder 12 which represents the useful volume of the syringe.

Care should of course be taken, when defining the production dimensions and tolerances of the various components, to ensure that the liner 20 can never abut against the end of the cylinder 11 or of the insert 5 before the lugs of the yoke have passed the curved tip 55.

In fact, should such a situation arise, the syringe would be irremediably unusable.

The difference in diameter between the cylinders 11 and 12 does not have any bearing on the working of the syringe embodying the invention and could, without departing from the scope of the invention, be left without further comment.

This difference is only provided so as to procure a syringe bearing a protective cover 4 for the needle 3 of uniform outer appearance.

In fact, as represented in FIG. 1, said protective cover 4 is, prior to utilization of the syringe, disposed around the cylinder 12. As the thickness of said cover 4 is identical to that of the insert 5, this provides a syringe of substantially constant outer diameter, with the exception of the gripping ribs 42.

The protective cover 4 comprises a slot 41 disposed axially and ending in an arc-shaped end.

A lug 13 disposed on the outer surface of the syringe body is intended to be positioned in said slot for the purpose of cooperating with it.

The syringe is provided in the disposition represented in FIG. 1 with the end piece 40 integral with the protective cover.

The user then removes said end piece 40, e.g., by imparting a rotational movement thereto, in order to reveal the needle 3.

As usual, the user then pulls the piston out to fill the syringe before pushing said piston back in. During this to-and-fro motion, the yoke turns as previously described in order to change the rack used and to prohibit any further outward pulling of the piston.

When the user has finished, he pulls the covers in such a way as to bring it into the position represented in FIG. 6 for which he puts the cover back on the soiled needle and throws the syringe away.

When said cover is removed, the lug 13 is brought into the end part of the slot 41. A rotational movement is thus necessary to bring the cover back around the syringe body, thus enabling any untimely baring of the needle to be avoided during subsequent manipulations of the syringe.

Subject to a few minor modifications, it is possible to adapt the syringe embodying the invention in order for it to be possible to market the syringe pre-filled, e.g., for vaccination products.

In order to ensure good preservation of the products, they must be packed in neutral materials such as glass. To this end, there is provided that a glass tank be used presenting a needle disposed through its base and that the syringe body be formed by duplicate moulding of said tank with a plastic material.

Figure 7:
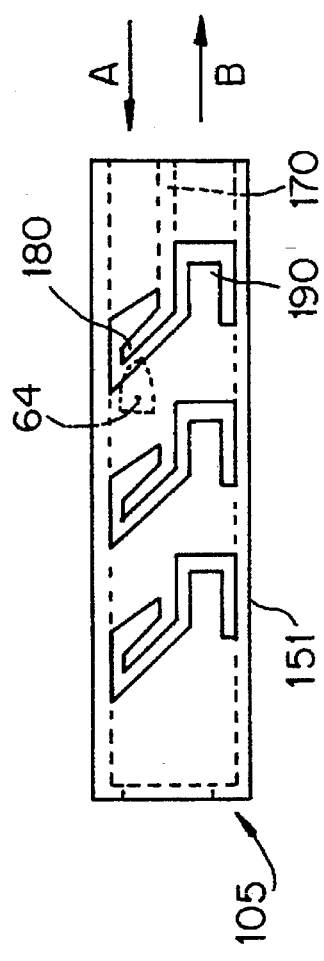
FIG. 7 is a detailed view of the body of the insert of a syringe embodying the invention enabling the injected product to be dosed.

FIG. 7 schematically represents a detailed view of the body 151 of the insert 105 used for a syringe embodying the invention enabling one single injection to be administered and having the possibility of dosing the product to be injected.

This body 151 has two racks 190 and 180, one with transversal tongues and the other with at least one oblique tongue, separated by a discontinuous longitudinal rib 170.

These racks are disposed in such a way that the ends of the tongues constituting them protrude inwardly of the body of the insert in order to cooperate with the lugs 63 and 64 borne by the yoke 6.

The rack 180 comprises, in the example represented, several oblique tongues, i.e., slanted in relation to the axis of the syringe in order to allow the piston to move outwards in direction A and to longitudinally prevent a direct return of the piston towards the bottom of the syringe body. The oblique tongues of this rack force the lug 64, which cooperates with them during the return movement of the piston towards the bottom of the syringe body, to have a circumferential motion moving it aside from the axis of the rack.

The tongues of the rack 180 are thus disposed so as to oblige the yoke 6 bearing the lug 64 to rotate about the axis of the piston in such a way as to bring said lug 64 into cooperation with the tongues forming the rack 190.

The rack 190 has transversal tongues for the purpose of allowing longitudinal displacement of the piston in direction B pointing towards the bottom of the syringe while prohibiting any longitudinal outward motion of said piston by abutment against the flat end 66 of the lug 64.

By way of such an arrangement, the user of the syringe draws the piston outwards from the body of the syringe in direction A until the useful volume of product has been drawn in.

At all times, once the lug 64 has gone past at least one of the oblique tongues of the rack 180, the user can push the piston back in to administer the injection. During this motion, the lug abuts against the tongue situated above the position to which it has been pulled. The tongue then deviates it, which makes the yoke rotate until said lug cooperates with the rack 190.

The motion in direction B then continues until the piston reaches the bottom of the syringe body.

As the rack 190 authorizes motion in direction B while preventing any motion in the opposite direction, it is thus completely impossible to reuse the syringe for a second injection.

The oblique tongues of the rack 180 can be provided spaced apart as represented in the drawing insofar as their task is to deviate the yoke in the direction of the rack 190 and not to block the downward motion of the piston as with the syringes proposed to date.

This space can be put to advantage by the user of the syringe in order to carry out to-and-fro motion with the piston enabling bubbles to be evacuated from the liquid drawn in. However, the space is sized small enough to prevent injection of any product from the syringe during the to-and-fro motion.

It should be noted that this to-and-fro motion is only possible between the position in which the lug 64 touches one of the tongues and the position in which the lug 63 touches the next tongue. In fact, when the lug 63 has passed the next tongue, the return motion of the piston towards the bottom of the syringe body is prohibited by jarring of said tongue between the two lugs 63 and 64 as long as the lug 64 has not also passed said tongue.

FIGS. 9 and 10 represent a syringe embodying the invention enabling two injections to be administered.

For each injection, it is necessary to have a couple of racks and a yoke rotatably mobile on the piston in order to be able to take up position in front of the second rack authorizing the downward return motion of the piston towards the bottom of the syringe body.

The syringe enabling two injections to be administered is then provided with two couples of racks arranged side by side.

A slanted tongue is disposed at the end of the second rack of the couple enabling the first injection to be administered in order to rotate the yoke in such a way that the lugs its bears come and engage with the first rack of the second couple.

In this case, the body 251 of the insert is separated into four parts by longitudinal ribs 71, 72 and 73 disposed on its inner wall and each ending respectively in an oblique tongue 81, 82 and 83.

Each part of the body 251 of the insert bears a series of tongues of which the ends protrude from the inner wall in the direction of the axis in order to form racks. The racks 91 and 93 are comprised of tongues arranged with their end sides pointing towards the end plate of the insert, whereas the racks 92 and 94 are comprised of tongues pointing in the opposite direction.

The curved tips 81, 82 and 83 are respectively such that their ends are disposed longitudinally to the front of the tongues forming the racks 91, 92 and 93.

In the example represented, the rack 93 is a rack with oblique tongues obliging the yoke to turn during cooperation between the lug 64 and each of the tongues. The oblique tongue 83 is then constituted by the last tongue of said rack 93.

During assembly, the insert is positioned around the piston rod bearing the yoke 6 in such a way that the lugs 63, 64 are axially aligned with the tongues forming the first rack 91.

As usual in using a syringe, the piston 2 is firstly pulled outwards from the syringe body in order to fill said body 10.

During this motion, the lugs 63 and 64 of the yoke 6 slide along the tongues forming the first rack 91 by moving in the direction A represented in FIG. 10. Any motion of the piston 2 in the opposite direction during the filling is prevented by the abutment of the flat end 65 of the lug 63 against the end of one of the transversal tongues forming said first rack 91.

The outward movement of the piston 2 continues until the yoke 6 comes into contact with the inner side of the end wall of the insert, the tip 81 moving aside as the lugs pass. In this position reached at the end of the stroke, the oblique tongue 81 extends axially in the prolongation of the lugs 63 and 64.

When the user pushes the piston 2 back downwards towards the inside of the body 10 of the syringe in order to empty it of its contents, the lug 64 comes into contact with the oblique tongue 81.

The tapered lug 64 then slides along the oblique tongue 81, thereby rotating the yoke 6 about the rod 24 until the lugs 63, 64 are axially opposite the tongues forming the second rack 92.

The piston 2 can then be pushed back in direction B while all withdrawal motion in direction A is prevented by the side 66 of the lug 64 bearing against the end of one of the transversal tongues forming the second rack 92.

This outward and inward motion of the piston 2 enables the first injection to be administered.

When the piston 2 is again at the bottom of the syringe body 10 after the first injection, the lugs 63 and 64 are axially aligned with the oblique tongue 82. When the piston 2 is again drawn outwards to draw in the product intended for the second injection, the lug 63 abuts against the oblique tongue 82, thereby again rotating the yoke 6 about the rod 24.

This rotating motion of the yoke brings the lugs 63, 64 into the axial prolongation of the rack 93.

The piston can then be drawn outwardly again in the direction of arrow A in order to fill the syringe with the required quantity of product, and then be pushed in again, the yoke 6 being rotated by one of the oblique tongues of the rack 93 so as to make the lugs engage with the fourth rack 94.

Irrespective of the position of the piston in relation to the syringe body 10 during a movement tending to push it towards the bottom of said body, all outward motion is blocked by the cooperation of the side 66 of the lug 64 with the end of the tongues forming the rack 92 or the rack 94. Should the user then attempt to overcome this blocking, the fragile link 25 breaks, thus rendering the syringe definitively unusable.

In the example represented, only the second injection can be administered with a chosen volume of product. This example corresponds to a large number of administrations for which the product to be injected is proposed in the form of two ingredients to be mixed. In these cases, all the liquid must generally be mixed with all the powder, even if the quantity to be injected into the patient is smaller.

It is, of course, possible to provide a syringe also enabling dosing of the liquid product to be used in the mixture by replacing the rack 91 having transversal tongues by a rack with oblique tongues.

When the syringe is constituted so as to enable the administration of two injections, it is possible to provide a double needle 300 comprised of two needles of which one is inserted into the other, a thin inner needle 301 welded to the end of the syringe body and a removable needle 303 of larger diameter positioned around said thin needle.

The lid of the flacon containing the liquid is thus pierced with the needle of large diameter, the mixture to be injected is prepared, and then the needle of large diameter is removed so as to bare and use the thin needle to inject the product into the patient.

Though this invention has been described in reference to drawings showing a syringe enabling two injections to be administered, it is, of course, possible to adapt the insert so as to provide additional racks and curved tips when the need is felt to provide syringes enabling the administration of a higher number of injections.

The number of injections that can be provided also depends on the circumferential dimension of the insert and therefore on the diameter of the syringe.

The assembly of a syringe embodying the invention has been described previously by positioning a subassembly comprised of the insert, piston and yoke in the syringe body and by making the insert integral with said syringe body.

As another embodiment, as represented in FIG. 11, the insert 105 is designed in the form of a portion of the body 100 of the syringe and is mounted and fitted on said body by any known means (welding, glue, etc.).

Accurate positioning of the insert is achieved by the engaging of slugs 150 in openings 101.

The insert is fitted onto the body subsequent to the positioning of the piston bearing the yoke inside said body.

I claim:

1. Syringe for administering a given number of injections comprising a body (10) in which is disposed a piston (2), of the kind comprising at least two racks (53, 54; 180, 190; 91, 92; 93, 94) borne by the body (10), one (53, 180, 91, 93) of these racks authorizing outward motion of the piston (2) and the other (54, 190, 92, 94) authorizing the return thereof towards a bottom of the body (10), and at least one lug borne by the piston (2) and driven in translation by the latter, each of said racks being capable of being shifted in a single direction in relation to a lug, and at least one needle (3) attached to an end of said body, wherein:

said racks (53, 54; 180, 190; 91, 92; 93, 94) are fitted onto the body (10), each rack having tongues, said racks (53, 54; 180, 190; 91, 92; 93, 94) are separated longitudinally by a rib (52, 170, 71, 72, 73) disposed onto the body (10), the piston (2) bears two lugs (63, 64), one lug (63) being intended to come into abutment against the tongues of a rack (53) in order to block all reverse motion of the piston (2) during filling of the syringe, the other lug (64) being intended to come into abutment against the tongues of the other rack (54) to prevent any withdrawal motion of the piston when the piston is pushed inward towards the bottom of the syringe, said lugs (63, 64) are borne by a yoke (6) which straddles the piston (2) and is rotatably mobile about the axis of said piston (2) so as to be driven in translation by the piston (2) while rotating freely in relation to the latter, a curved tip or oblique tongue (55, 81, 83) is formed at an end of the rib (52, 71, 73) so as to bring the lugs (63, 64) opposite the rack enabling the piston (2) to return towards the bottom of the syringe body.

2. Syringe as claimed in claim 1, wherein the rack authorizing the outward motion of the piston (2) comprises at least one tongue which is oblique in relation to the axis of the syringe so as to enable it to be passed by the lugs (63, 64) of the yoke (6) during the outward motion of the piston, and to impose upon the yoke (6), during the inward motion of the piston, a rotating motion so as to position the lugs (63, 64) of the yoke (6) opposite the tongues of the second rack (190) in such a way that it will be possible to push in the piston when each of the oblique tongues of the rack have been passed over.

3. Syringe as claimed in claim 1, comprising several couples of alternate racks (91, 92; 93, 94), the first rack (91) allowing the piston (2) to move outwards from the body of the syringe, and the last rack (94) enabling the piston (2) to be driven back towards the bottom of the syringe body, and oblique tongues (81, 82, 83) situated at the end of each rack excepting the last rack to ensure the rotation of the yoke (6) so that the lugs (63, 64) cooperate with the next rack every time the direction of displacement of the piston is reversed.

4. Syringe as claimed in claim 3, wherein at least one of the alternate racks has all oblique tongues and a remainder of the alternate racks include at least one transversal tongue.

5. Syringe as claimed in claim 3, wherein said needle comprises a thin internal needle (301) welded to the end of the syringe body and a removable needle (303) of larger diameter positioned around said thin needle so as to administer to the patient the injection with the thin needle.

6. Syringe as claimed in claim 1, wherein the yoke (6) is of globally U-shaped cross section and bears said lugs (63, 64) on its outer side in the rounded portion of the "U" shape.

7. Syringe as claimed in claim 6, wherein the ends of said "U" shape are bordered by ribs (61, 62) on their outer surfaces.

8. Syringe as claimed in claim 1, wherein at least one of the two lugs (63, 64) is tapered in a direction of an axial end of the yoke (6).

9. Syringe as claimed in claim 1, comprising an insert (5, 105) fitted onto the body (10), the racks (53, 54; 180, 190; 91, 92; 93, 94) being formed on the insert (5, 105).

10. Syringe as claimed in claim 9, wherein the insert (5) is comprised of a semi-cylindrical body (51) ended by an end plate (50) perpendicular to it.

11. Syringe as claimed in claim 10, wherein the body (51) of the insert (5) is separated, by the rib (52) disposed on an inner wall of the body ending in the curved tip (55) extending into a recess (56), into two parts each bearing a series of tongues whose ends protrude from the inner wall in the direction of the axis in order to confer upon said body (51) a longitudinal section in the shape of racks (53, 54).

12. Syringe as claimed in claim 11, wherein the curved tip (55) has its end disposed longitudinally to the front of the tongues forming the rack (53) authorizing outward motion of the piston (2).

13. Syringe as claimed in claim 11 to wherein a distance axially separating the inner side of the end plate (50) of the insert (5) from the end of the curved tip (55) is greater than the length of the yoke (6) so that, when the outward pulling motion of the piston is completed, the yoke (6) is completely disposed between the end plate (50) and said tip (55) extends axially in the prolongation of the lugs (63, 64), and so that, during the return motion of the piston (2) towards the inside of the syringe body (10), the lug (64) comes into contact with said curved tip (55) and rotates the yoke (6) to bring the lugs (64, 63) into the axis of the tongues forming the rack (54) authorizing the return motion of the piston towards the bottom of the syringe body, without the piston being rotated.

14. Syringe as claimed in claim 1, wherein the piston (2) comprises two portions (22, 23) connected together by a cylindrical axial rod (24).

15. Syringe as claimed in claim 14, wherein said cylindrical axial rod (24) is separated into two parts by a fragile link (25).

16. Syringe as claimed in claim 14, wherein the diameter and length of said axial rod (24) are such that the yoke (6) can be positioned thereupon in such a way as to straddle it.

* * * * *